(12) United States Patent
Spehalski et al.

(10) Patent No.: US 6,478,789 B1
(45) Date of Patent: Nov. 12, 2002

(54) WOUND DRAIN WITH PORTALS TO ENABLE UNIFORM SUCTION

(75) Inventors: Stephen R. Spehalski, Gurnee, IL (US); David Brown, Gurnee, IL (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 09/440,445

(22) Filed: Nov. 15, 1999

(51) Int. Cl.$^7$ .............................................. A61M 25/00
(52) U.S. Cl. ........................ 604/540; 604/93; 604/280; 604/264
(58) Field of Search ............................. 604/27, 35, 43, 604/45, 500, 508, 129, 264, 266, 523, 540, 541–544, 93.01

(56) References Cited

U.S. PATENT DOCUMENTS

| | | |
|---|---|---|
| 105,038 A | 3/1870 | Liddell |
| 1,596,754 A | 8/1926 | Moschelle |
| 1,879,249 A | 9/1932 | Honsaker |
| 2,134,152 A | 10/1938 | Schwarzmayr |
| 2,450,217 A | 9/1948 | Alcorn |
| 3,260,258 A | 7/1966 | Berman |
| 3,582,234 A | 6/1971 | Mamaroneck et al. |
| 3,590,820 A * | 7/1971 | Nehra et al. ................. 604/268 |
| 3,599,641 A | 8/1971 | Sheridan |
| 3,623,484 A | 11/1971 | Schulte |
| 3,630,206 A | 12/1971 | Gingold |
| 3,630,207 A | 12/1971 | Kahn et al. |
| 3,860,008 A | 1/1975 | Miner et al. |
| 3,993,080 A | 11/1976 | Loseff |
| 4,007,743 A | 2/1977 | Blake |
| 4,089,506 A | 5/1978 | Blake |
| 4,307,723 A | 12/1981 | Finney |
| 4,398,910 A * | 8/1983 | Blake et al. ................. 604/93 |
| 4,429,693 A | 2/1984 | Blake et al. |
| 4,465,481 A | 8/1984 | Blake |
| 4,508,533 A | 4/1985 | Abramson |
| 4,523,920 A | 6/1985 | Russo |
| 4,573,965 A | 3/1986 | Russo |
| D288,962 S | 3/1987 | Blake |
| 4,650,463 A | 3/1987 | Leveen et al. |
| 4,676,530 A | 6/1987 | Nordgren et al. |
| 4,717,379 A | 1/1988 | Ekholmer |
| 4,753,640 A | 6/1988 | Nichols et al. |
| 4,976,684 A | 12/1990 | Broadnax, Jr. |
| 4,995,863 A | 2/1991 | Nichols et al. |
| 5,035,764 A | 7/1991 | Blake |
| 5,116,310 A * | 5/1992 | Seder et al. ................... 604/43 |
| 5,140,983 A | 8/1992 | Jinotti |
| 5,160,325 A | 11/1992 | Nichols et al. |
| 5,242,720 A | 9/1993 | Blake |
| 5,360,414 A * | 11/1994 | Yarger ......................... 604/264 |
| 5,380,314 A | 1/1995 | Herweck et al. |
| 5,511,965 A | 4/1996 | Batdorf et al. |
| 5,549,579 A | 8/1996 | Batdorf et al. |
| 5,562,622 A | 10/1996 | Tihon |
| 5,817,071 A | 10/1998 | Dewindt et al. |
| 6,099,513 A * | 8/2000 | Spehalski .................... 604/264 |

FOREIGN PATENT DOCUMENTS

FR        2240026        6/1973

* cited by examiner

Primary Examiner—Brian L. Casler
Assistant Examiner—Jennifer J. Maynard
(74) Attorney, Agent, or Firm—Andrew G. Rozycki

(57) ABSTRACT

The present invention is directed to a wound drain including a plurality of ducts 24, a plurality of lumens 26 and a plurality of portals 28. The ducts 24 provide an entrance for exudate from the wound site into the wound drain. The lumens 26 and ducts 24 provide drainage channels for exudate from the wound site. The portals 28 provide fluid communication between the ducts 24 and the lumens 26. The portals on the wound drain are adapted and arranged to provide uniform suction along the length of the wound drain.

61 Claims, 7 Drawing Sheets

WOUND DRAIN WITH PORTALS TO ENABLE UNIFORM SUCTION

FIELD OF THE INVENTION

The present invention relates to implantable wound drains.

BACKGROUND OF THE INVENTION

Generally wounds resulting from surgical procedures are either closed at the end of the surgical procedure or allowed to close in the course of the body's natural healing process. Surgical wounds typically produce a fluid commonly referred to as exudate. Therefore whenever surgical wounds are closed, a means must be provided to drain the accumulating exudate from the site of the wound to promote satisfactory healing.

Many prior art wound drain devices have attempted to provide adequate drainage for surgical wounds. One such prior art device includes a drain section consisting of a length of tubing perforated with small holes through the tubing wall. Exudate from the surgical wound typically enters the tubing through the small holes and is suctioned away from the wound via the tubing lumen. However, the use of a single lumen increases the likelihood of clogging resulting from debris or new tissue ingrowth entering through the small holes. In addition, the structural weakness of the walls of the tubing often leads to the formation of kinks.

Another prior art wound drain device consists of a central core with radially projecting strut portions. The strut portions are equal in size and are spaced at equal angles relative to one another. The periphery of the wound drain is defined by a plurality of overhang portions at the end of each of the four strut portions, thereby forming four T-shaped members. The overhang and strut portions cooperate to form four longitudinal lumens extending the length of the drain. This prior art design does not provide for the even distribution of suction over the length of the wound drain.

Yet another prior art surgical wound drain device includes a pair of spaced apart flanges with a web disposed therebetween having a single longitudinal lumen with apertures formed transversely through the flanges and intersecting the lumen. Not only does the use of a single lumen design increase the likelihood of blockages, this design does not enable the even distribution of suction throughout the length of the drain.

Another prior art wound drain device consists primarily of a triple lumen catheter body. A three-tube connector having a suction port, an irrigation port and an air intake port is adapted for connection to the catheter body at its proximal end. This prior art design is susceptible to fluid back ups causing clogging and lose of air venting capabilities. Additionally, the three lumens require a larger opening in the wound often leading to greater patient discomfort.

Another prior art wound drain device includes two lumens. The first lumen is used for applying suction to a wound area. A check valve element and an antibacterial filter are positioned in line communication with a second lumen to prevent backflow of fluids through the second lumen into the filter. This design does not provide for the even distribution of suction over the length of the wound drain.

Yet another prior art device consists of a perforated tubing for surgical drainage applications. The tubing is comprised of a body having a central passageway in the clover-leaf cross-sectional appearance with four longitudinally extending grooves spaced at ninety degree arcuate intervals about the body. Perforations interconnect the grooves with the passageway. The perforations are in the form of a series of holes in the bottoms of the grooves. The use of a central passageway increases the likelihood of clogs occurring.

Another prior art wound drain device consists of multiple parallel lumens to convey fluid away from a surgical wound. This design includes a plurality of holes and at least one longitudinal slot extending interiorly from the outside surface which admits fluids into the lumens. Internal holes divert fluid away from blocked lumens. The external holes and slots are susceptible to new tissue ingrowth. Additionally, uniform suction is not present throughout the length of the wound drain.

Thus what is needed is a device which provides for the adequate drainage of exudate from surgical wounds. The device should be designed to maximize the drainage of exudate while minimizing the possibility of tissue ingrowth. The device should further provide generally consistent suction throughout the length of the device and minimize patient discomfort with a streamline design.

SUMMARY OF THE INVENTION

The present invention provides a wound drain device which enables the adequate drainage of exudate from surgical wounds. The present invention is designed to maximize the drainage of exudate while minimizing the possibility of tissue ingrowth. The present invention further provides generally consistent suction throughout the length of the wound drain. Additionally patient discomfort is minimized as the present invention has a relatively streamline design.

The present invention is directed to a wound drain including a plurality of ducts, a plurality of lumens and a plurality of portals. The ducts provide an entrance for exudate from the wound site into the wound drain. The lumens provide drainage channel for exudate from the wound site. The portals provide fluid communication between the ducts and the lumens. The portals are adapted and arranged to approximately provide uniform suction along the length of the wound drain.

The distance between adjacent portals may be varied such that the distance between portals positioned further away from the suction source is less than the distance between the portals positioned closer to the suction source. The portals may vary in size such that the portals closer to the suction source are smaller in size than the portals located further away from the suction source.

DESCRIPTION OF THE PREFERRED EMBODIMENTS

Figure 1:
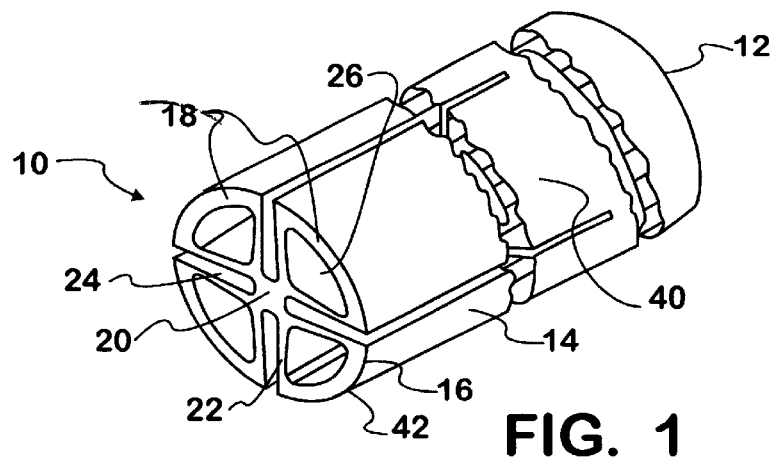
FIG. 1 is a perspective view of a preferred embodiment of a round wound drain made in accordance with the principles of the present invention.

Referring to FIG. 1, a perspective view of a preferred embodiment of an implantable wound drain for drainage of fluid from a surgical site or wound of a patient made in accordance with the principles of the present invention is seen. This implantable wound drain includes an implantable segment 10 that is designed for use with a transition segment 12 and a single lumen segment (not shown). The implantable segment 10 provides a pathway from the wound site to the interior of the wound drain. The transition segment 12 is in fluid connection with the implantable segment 10 and is positioned external to the body of the patient. The single lumen segment receives the fluid from the transition segment and is in fluid connection with the suction source (not shown).

Figure 2:
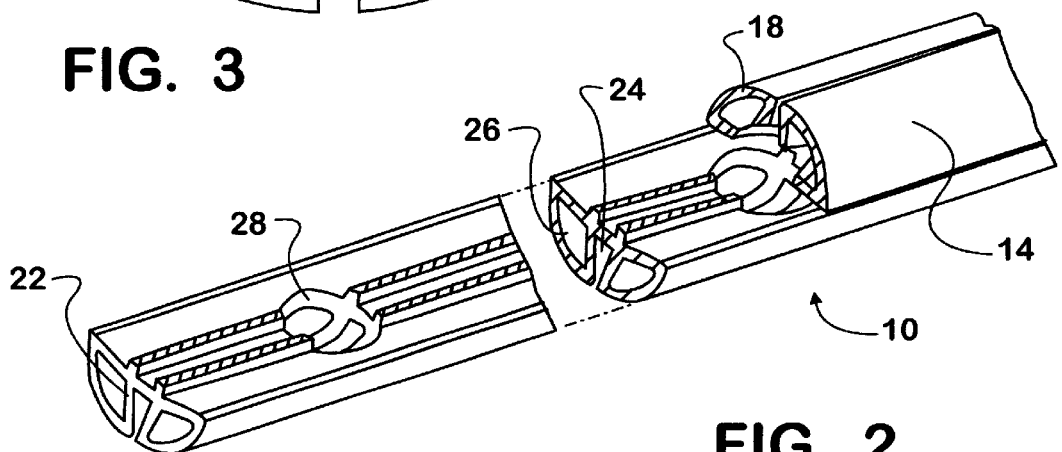
FIG. 2, a perspective view of the round wound drain of FIG. 1 with portions broken away to reveal the interior.

A round implantable segment 10 has an elongated tubular body 14 consisting primarily of an annular outer wall 16 divided into a plurality of segments 18; a central core 20 located radially inward from the outer wall 16; a plurality of radial inner walls 22 extending between the central core 20; and the outer wall 16 and a plurality of interior portals 28 (shown in FIG. 2). The annular outer wall 16 has a generally circular cross-sectional shape. The central core 20 and inner walls 22 extend along the longitudinal axis of the tubular body 14. Each segment 18 of the outer wall 16 is integrally connected to a pair of inner walls 22. The inner walls 22 are also integrally connected to the central core 20.

Referring now to FIG. 2, a perspective view of the implantable segment 10 is shown with portions broken away to reveal the interior of the implantable segment 10. The implantable segment 10 generally includes a plurality of elongated ducts 24, a plurality of lumens 26 and a plurality of portals 28. In a preferred embodiment, the portals 28 are of different sizes. The ducts 24 provide access for the exudate to flow from the wound site into the implantable segment 10. The portals 28 provide fluid connection from the ducts 24 to the lumens 26. The ducts 24 and lumens 26 provide flow paths for the exudate to exit.

Figure 3:
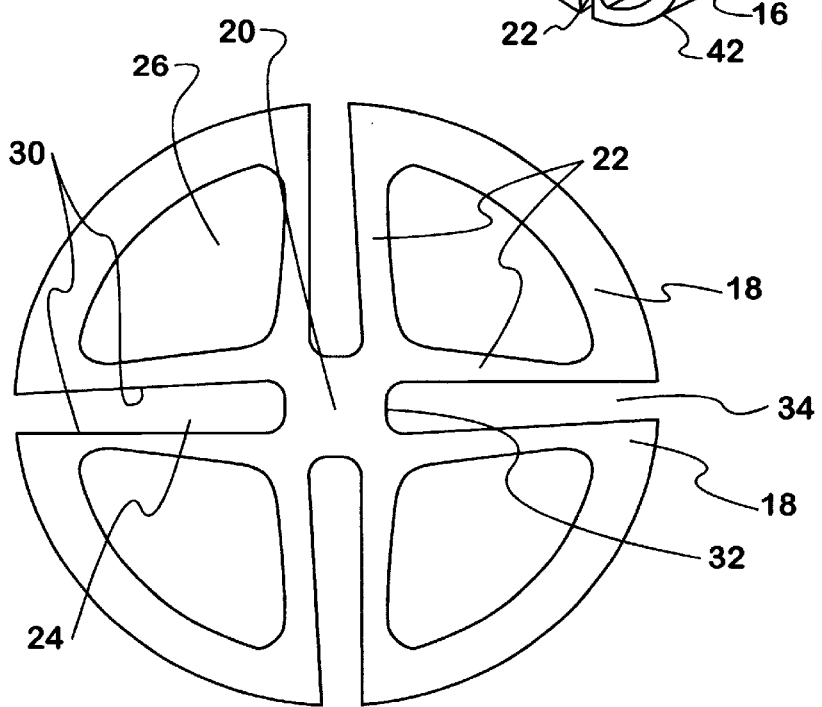
FIG. 3 is an enlarged cross-sectional slice of the round implantable segment of FIG. 1.

As shown in FIG. 3, each lumen 26 is defined by the area enclosed within a pair of inner walls 22 connected to a segment 18 of the outer wall and the central core 20. In the embodiment described herein, the lumens 26 are generally triangular in shape. The lumens 26 extend the length of the tubular body 14 of the implantable segment 10. In an alternative embodiment of the invention, a central generally square shaped lumen running within the central core 20 along the length of the tubular body 14 is provided in addition to the generally triangular shaped perimetrically arranged lumens 26. Alternative shapes of a central lumen running within the central core 20 along the length of the tubular body 14 are also considered to be within the scope of the present invention.

The elongated ducts 24 also extend across the length of the tubular body 14. The opposing interior side walls 22 of the ducts 24 are defined by the outer surface 30 of the inner walls 22 of adjacent lumens 26. Each elongate duct 24 has a duct base 32 and a duct entrance 34. The duct base 32 has a generally shallow U-shape and is located adjacent the central core 20. The duct entrance 34 is defined by the area between the segments 18 of the outer wall 16. In an alternative embodiment, the duct base 32 may have a generally shallow V-shape.

The width of each duct entrance 34 is substantially smaller than the maximum width of a lumen 26. In addition, the maximum width of a duct entrance 34 is smaller that the width of a duct base 32. Thus, the opposing interior side walls 22 of each duct 24 converge towards one another as they extend outwardly from the duct base 32 toward the duct entrance 34. The converging nature of the opposing side walls 22 of each duct 24 provides sufficient access for exudate to flow into the implantable segment 10 but limits access for tissue growth to enter the duct 24. Although the preferred embodiment describes elongated ducts 24 characterized by converging opposing side walls 22, other configurations of ducts including but not limited to those having parallel opposing side walls are considered to be within the scope of the invention.

Figure 5:
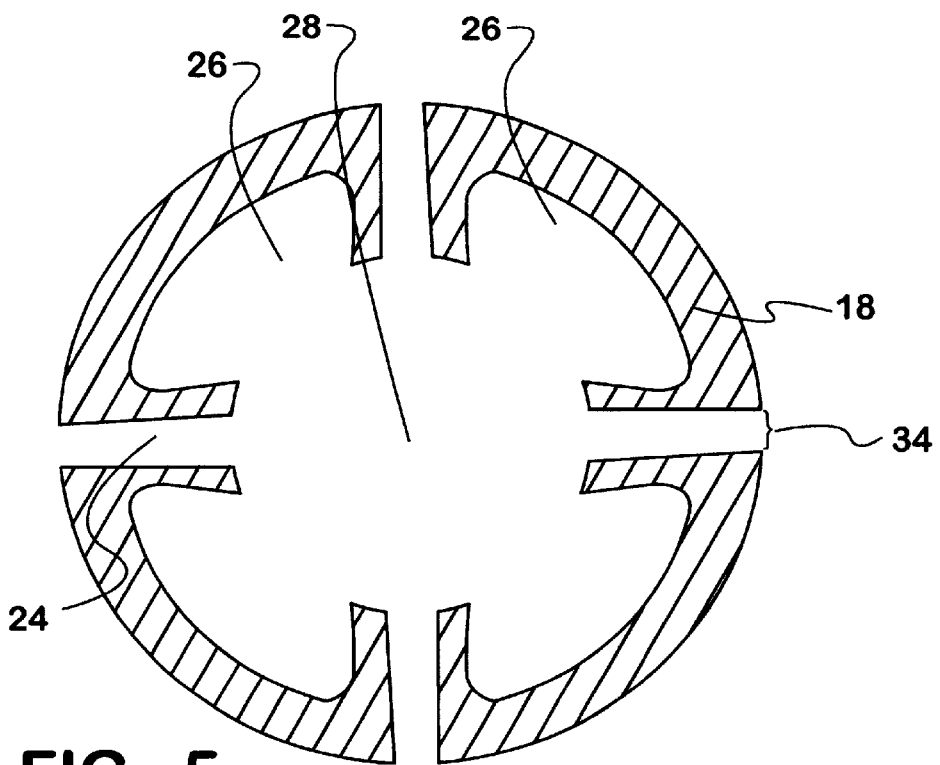
FIG. 5 is an enlarged cross-sectional slice of the implantable segment of FIG. 1 showing an alternative embodiment of portals.
Figure 4:
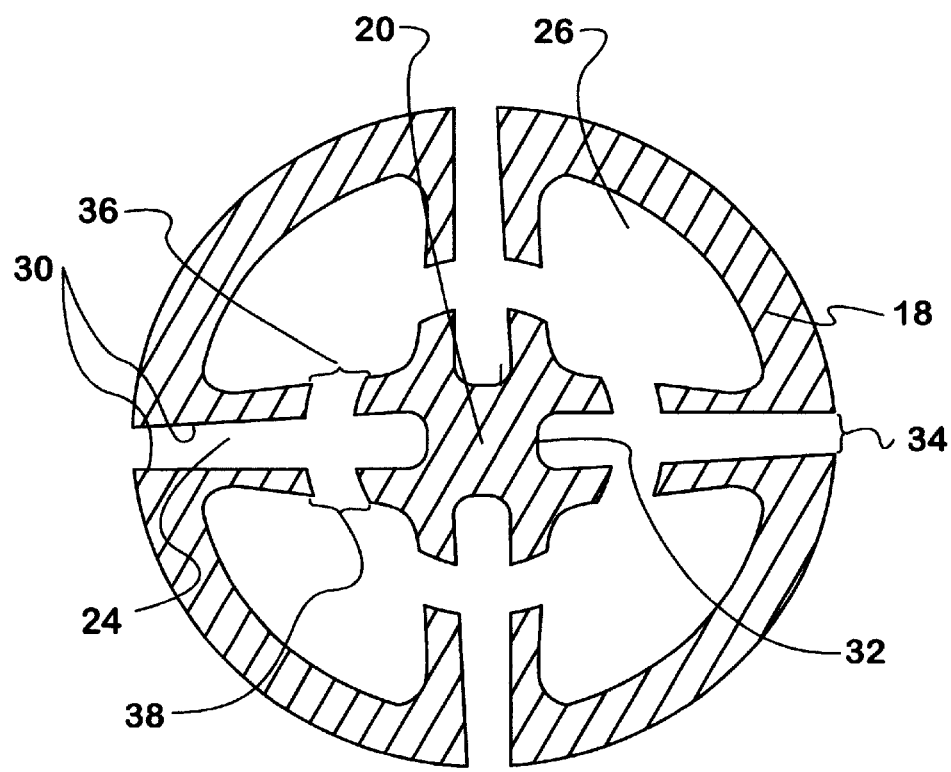
FIG. 4 is an enlarged cross-sectional slice of the implantable segment of FIG. 1 illustrating an embodiment of portals.

The implantable segment 10 includes a plurality of interior portals 28. The portals 28 provide fluid connection from the ducts 24 to the lumens 26. In one embodiment of the interior portal 28, shown in FIG. 4, each duct has two pathways 36, 38 providing access to two adjacent lumens 26. An alternative embodiment of the interior portals 28 is shown in FIG. 5. In this embodiment, each duct 24 is in fluid communication with all of the lumens 26. Both embodiments of the portals 28 provide collateral drainage paths for the exudate exiting the wound site should a lumen 26 become occluded.

The entrances 34 of the narrow ducts 24 through the outer wall 16 permit fluid flow from the wound site exteriorly of the drain 10 through the duct entrances 34 into the duct 24. The interior portals 28, which are not exposed at the exterior surface of the outer wall 16 of the implantable segment 10, then provide multiple collateral drainage paths for fluid flow from the ducts 24 to the lumens 26 in the event clogging of any of the lumens 26 should occur. While the ducts 24 provide fluid communication from the wound into the implantable segment 10, the ducts 24 also provide a means of offsetting the tissue from the interior portals 28. The portals 28 are disposed closer to the duct bases 32 and to the inner end of each lumen 26 than to the duct entrances 34. The portals 28 are placed at such interior locations to prevent the growth of tissue into the lumens 26.

Figure 14:
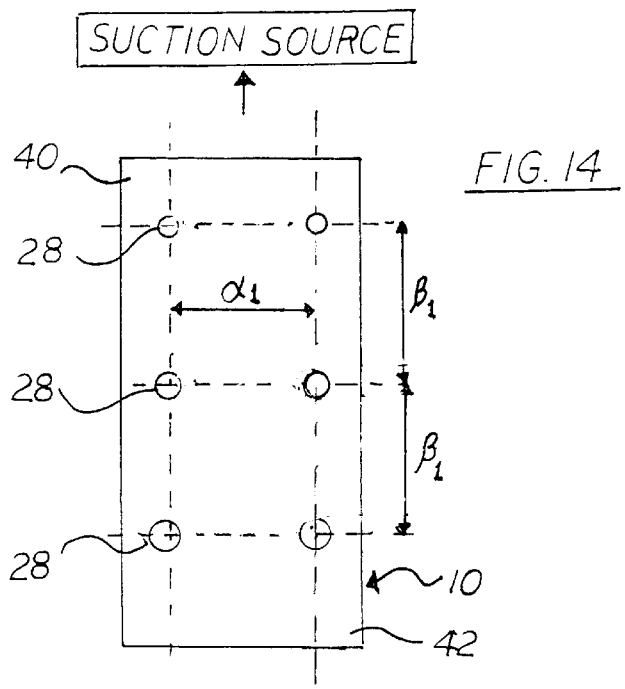
FIG. 14 is a schematic illustration of the relationship between the portals and the suction source in accordance with one embodiment of the invention.
Figure 16:
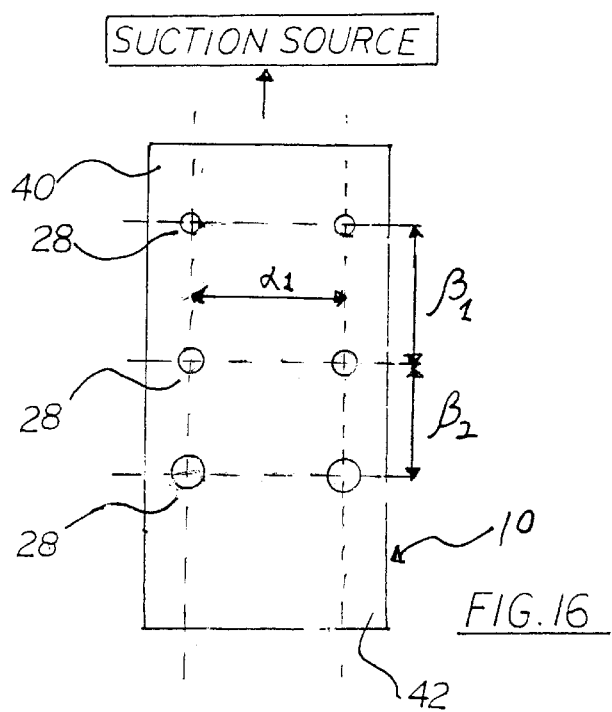
FIG. 16 is a schematic illustration of the relationship between the portals and the suction source in accordance with one embodiment of the invention.

The size of each portal 28 and its distance from the suction source determine the amount of suction present. Typically less suction is present at sites with smaller size portals 28 and more suction is present at sites with larger size portals 28. In the preferred embodiment of the invention, portals 28 of a smaller size are placed at the proximal end 42 of the implantable segment 10 and larger size portals 28 are placed at the distal end 42 of the implantable segment 10. Increasing the portal size as a function of the distance of the portal 28 from the suction source produces an implantable segment 10 which has a more uniform suction force along the entire length of the implantable segment 10 body. This embodiment is schematically illustrated in FIGS. 14 and 16, wherein size of the portals 28 increase toward the distal end 42 of an implantable segment 10 of the wound drain.

A preferred embodiment of a round implantable segment 10 includes a total of eight portals 28. The diameter for each of the eight portals 28 can be determined using a two step process. The first step determines the hydraulic diameter of the portal 28 to lumen 26 hole ($d_{hole}$) connecting the lumen 26 to the portal 28 in inches in accordance with the following:

$$d_{hole}=0.5482(A/P)+(6.4852+10^{-4})(A/P)(L_T-L)^3$$

where:

A is the cross-sectional area of the lumen (inches$^2$);

P is the perimeter of the lumen (inches);

$L_T$ is the total length of the drain (inches); and

L is the length from the open end of the implantable segment to the portal center (inches).

The second step determines the diameter of the portal ($d_{portal}$) in inches in accordance with the following:

$$d_{portal}=0.015+3.49(T_{iw})+0.9(d_{hole})$$

where:

$T_{iw}$ is the inner wall thickness (inches).

While the two step process for determining the portal 28 diameter for a round implantable segment 10 having eight portals 28 has been described, round implantable segments 10 having alternative numbers of portals 28 are also considered to be within the scope of the present invention. Processes analogous to the one disclosed, used to determine the portal 28 diameters for round implantable segments 10 having alternative numbers of portals 28 are also considered to be within the spirit of the present invention.

In operation, exudate from the wound site enters the multiple elongated narrow ducts 24 at any point along the implantable segment 10. The exudate is drawn toward the suction source via the path of least resistance, either flowing through the ducts 24 or entering the lumens 26 through the plurality of interior portals 28. The plurality of interior portals 28 gradually increase in size from the proximal end 40 of the implantable segment 10 to the distal end 42 of the implantable segment 10 deeper into the wound site. The increase in portal size is designed to compensate for the decrease in suction farther from the suction source. This results in a more effective distribution of suction and fluid flow throughout the entire length of the implanted implantable segment 10.

Should a duct 24 or a lumen 26 become blocked with an obstruction, the internal portals 28 provide alternate pathways for suction and fluid flow around the blockage through other open ducts 24 or lumens 26. This ensures the uninterrupted drainage of exudate from the patient's wound.

Figure 6:
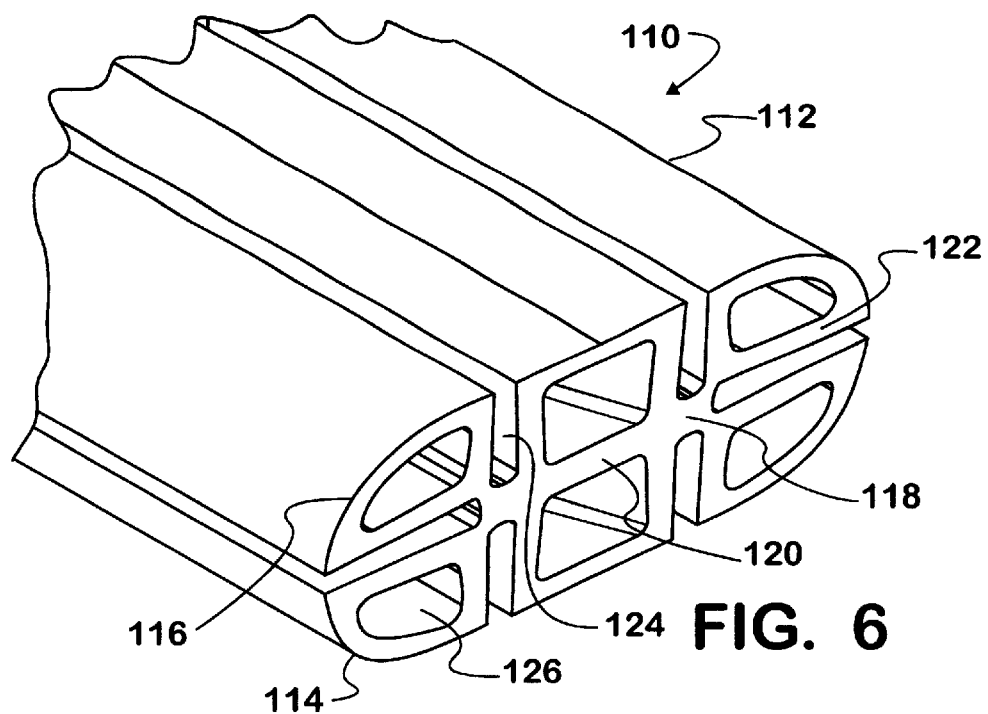
FIG. 6 is a fragmentary perspective view of an alternative embodiment of a flat wound drain made in accordance with the principles of the present invention.

Referring now to FIG. 6, an alternative embodiment of a implantable segment made in accordance with the principles of the current invention is designated generally 110. This alternative embodiment establishes a flat implantable segment 110. The implantable segment 110 has an elongated tubular body 112 and includes a generally oblong shaped annular wall 114 divided into a plurality of segments 116. Two centrally positioned cores 118 are laterally spaced in parallel relation to one another by an interior septum-like wall 120 and extend the length of the tubular body 112. A plurality of inner walls 122 also run the length of the tubular body 112 and extend between one of the central cores and the outer wall. A plurality of interior portals 128 (shown in FIG. 8) of different sizes are positioned along the implantable segment 110. Each segment of the outer wall 116 is integrally connected to a pair of inner walls 122. The inner walls 122 are integrally connected one of the central cores 118.

The flat implantable segment 110 generally includes a plurality of elongated ducts 124, a plurality of lumens 126 and a plurality of portals 128 of different sizes. The ducts 124 provide access for the exudate to flow from the wound site into the implantable segment 110. The portals 128 provide fluid connection from the ducts 124 to the lumens 126. The ducts 124 and the lumens 126 provide flow paths for the exudate to exit the implantable segment 110.

Figure 7:
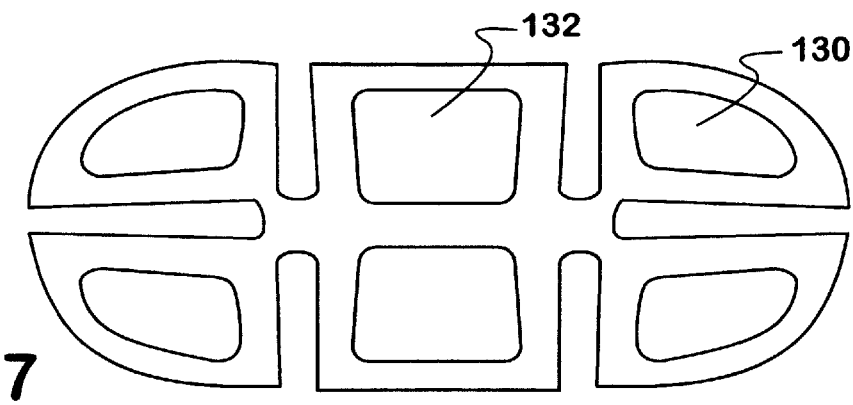
FIG. 7 is an enlarged cross-sectional slice of the flat implantable segment of the flat wound drain of FIG. 6.
Figure 8:
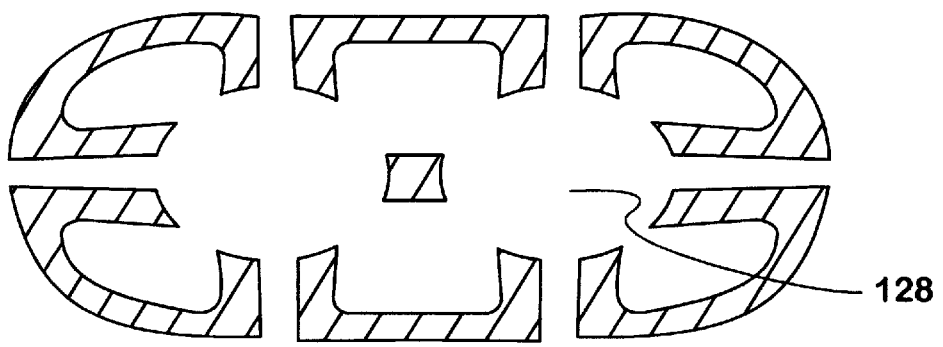
FIG. 8 is an enlarged cross-sectional slice of the flat implantable segment of the flat wound drain of FIG. 6 showing an embodiment of portals.

Referring now to FIG. 7, the flat implantable segment 110 has a generally oblong cross-sectional shape. The lumens 130 located at outer perimeter of the implantable segment 110 have a generally triangular shape and the more centrally located lumens 132 have a generally square shape. The square lumens 132 are primary contributors to the fluid dynamics effecting the hole diameter. All of the lumens 126 extend the length of the implantable segment 110. FIG. 8 is a cross-sectional slice of the flat implantable segment illustrating an embodiment of the interior portals 128.

A preferred embodiment of a flat implantable segment 110 includes a total of twelve portals 128. Six portals 128 are positioned on either side of the flat implantable segment 128. The diameter for each of the twelve portals 128 can be determined using a two step process. The first step correlates the hydraulic diameter of the hole ($d_{hole}$) connecting the lumen 126 to the portal 128 in inches in accordance with the following:

$$d_{hole} = \frac{0.1823\left(P_S/A_S\right)^{0.5}}{L^{0.63}}$$

where:

$A_S$ is the cross-sectional are of the "square" lumen 132 (inches$^2$);

$P_S$ is the perimeter of the "square" lumen 132 (inches); and

L is the length from the open end to the portal 128 center (inches).

The second step determines the diameter of the portal 128 ($d_{portal}$) in inches in accordance with the following:

$$d_{portal}=3.2052(T_{iw})+0.866(d_{hole})$$

where:

$T_{iw}$ is the inner wall 122 thickness (inches).

While the two step process for determining the portal 128 diameter for a flat implantable segment 110 having twelve portals 128 has been described, flat implantable segments 110 having alternative numbers of portals 128 are also considered to be within the scope of the present invention. Processes analogous to the one disclosed, used to determine the portal 128 diameters for flat implantable segments 110 having alternative numbers of portals 128 are also considered to be within the spirit of the present invention.

Figure 15:
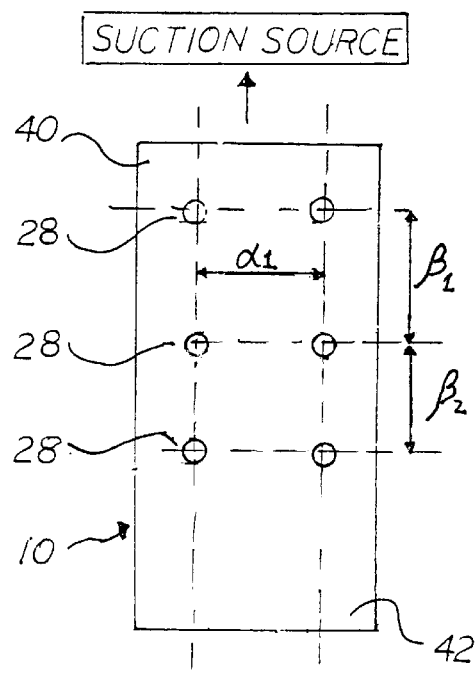
FIG. 15 is a schematic illustration of the relationship between the portals and the suction source in accordance with one embodiment of the invention.

In an alternative embodiment of the present invention, interior portals represented in FIGS. 14 and 16 as $\alpha_1$, $\beta_1$ and $\beta_2$ is varied as a function of the distance of the portals from the suction source. For example, the distance between adjacent portals closer to the suction source is greater than the distance between adjacent portals further away from the suction source. As a result the distal end of the implantable segment has more densely positioned portals than the proximal end of the implantable segment. This strategic placement of portals ensures approximately uniform suction force along the entire length of the implantable segment. This embodiment is schematically illustrated in FIG. 15 and 16, wherein the distance between the portals 28 decreases toward the distal end 42 of an implantable segment 10 of the wound drain.

While preferred embodiments of the invention have been disclosed, other variations in portal size, shape, placement and number are also considered to be within the scope of the invention. For example, the portals may be grouped into sets of two or more portals where the individual portals in each set are the same size. Those sets of portals positioned closer to the suction source are smaller in size than those sets of portals positioned further away from the suction source. Additionally other modifications of the implantable segment may include variations in the number of lumens, ducts and/or portals without departing from the spirit of the invention.

Preferred embodiments of the implantable segment can be manufactured using any suitable conventional fabrication technique, such as for example extrusion. The preferred embodiment of the implantable segment is made of a substantially pliable material. Such pliable materials may include, but are not limited to, a low durameter plastic or silicone ranging from about 40 Shore A to about 70 Shore A. The preferred embodiment of the round implantable segment is typically manufactured in three sizes, 10Fr., 15Fr. and 19Fr., but can be manufactured in other sizes without departing from the spirit of the invention. Alternative extrusion techniques such as for example, the use of an extrusion profile that is hubbed to a single lumen tube rather than produced by a unitary extrusion technique also may be employed.

The segments of the wound drain, the implantable segment, the transition segment and the single lumen segment can also be manufactured in a continuous extrusion process. When the required length of the implantable segment has been extruded the transition segment is then formed. As the extrusion process progresses, the entrances to the ducts are filled with material to form the outer wall with an uninterrupted perimeter. The lumens now created by the enclosed ducts in the transition segment are in communication with the ducts of the implantable segment. When the transition segment is complete, the extrusion die discontinues the central core and radial inner walls such that only one lumen remains and it is in communication with all transitional lumens. The single lumen segment is in the form of a cylindrical tube. This mode of extrusion has been called "unitary" extrusion. For the oblong shaped drain, following the transition segment, the tubular segment may be attached via a hub (adapter). The tubular segment will be of sufficient length to provide effective connection to a suction source.

Figure 9:
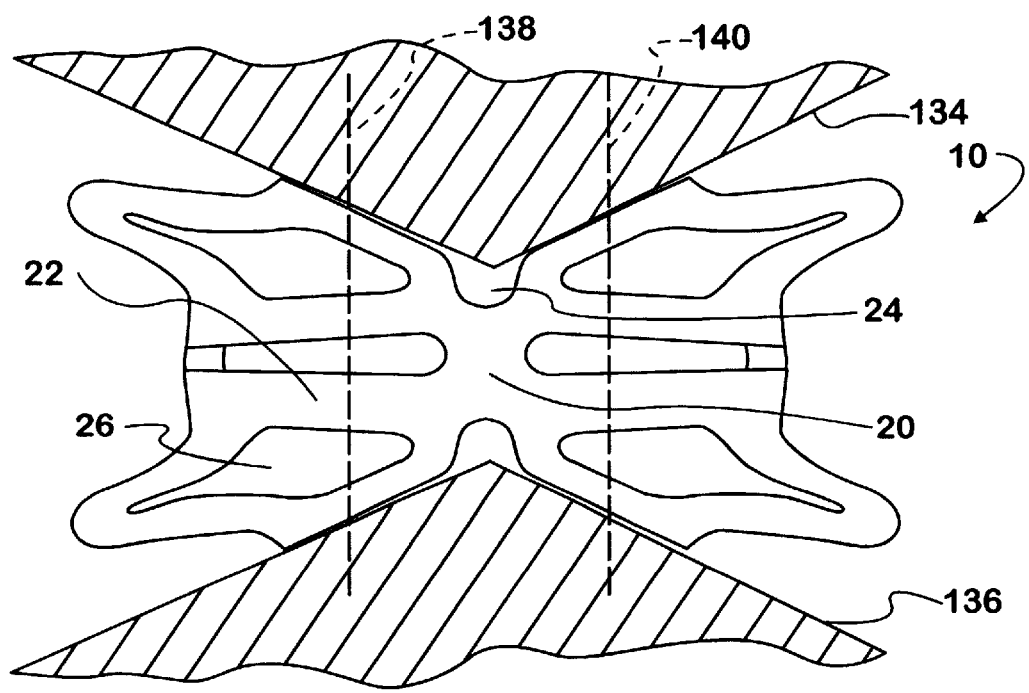
FIG. 9 is an enlarged and elevational view showing the formation of portals in a round implantable segment having a central core.
Figure 10:
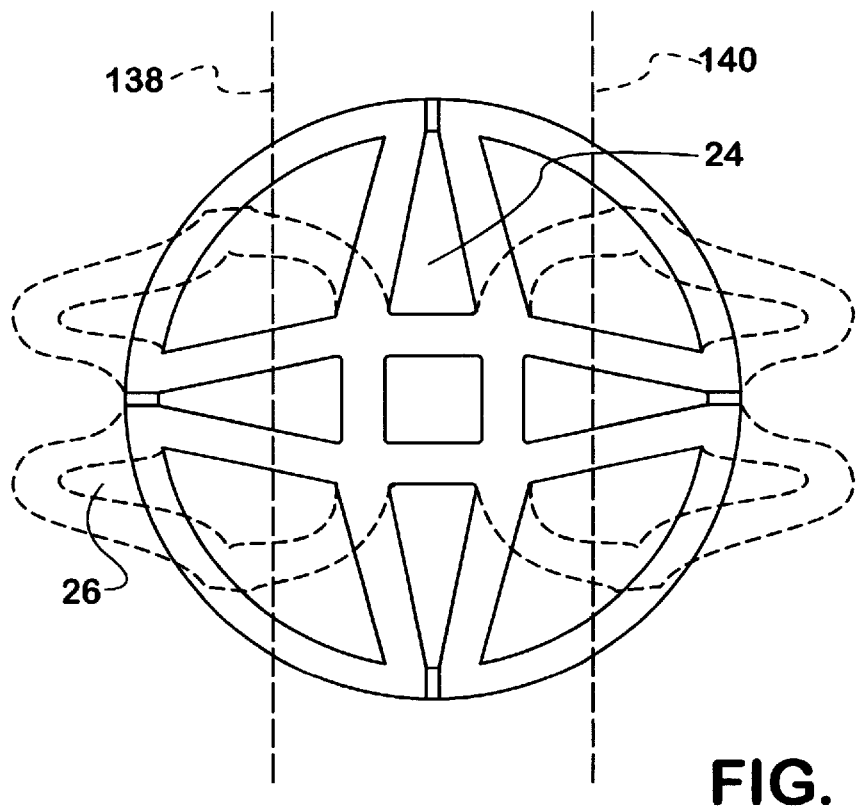
FIG. 10 is an enlarged and elevational view showing the formation of portals in a round wound drain including a generally square shaped lumen extending the length of the central core.

An exemplary technique for creating portals 28 in the round implantable segment 10 having a solid central core 20 is shown in FIG. 9. Following extrusion of the round implantable segment 10, a pair of opposing wedge-shaped dies 134, 136 are used to spread open an opposing pair of the ducts 24 on the same plane of symmetry. FIG. 9 depicts the general shape of the round implantable segment 10 following such spreading by the opposing wedge-shaped dies 134, 136. Thereafter, the portals 28 are punched by conventional dies (not shown) preferably through the side walls 22 and the central core 20, removing the material located between the parallel dashed lines 138, 140. All lumens 26 and ducts 24 are thereby traversed to provide for maximum number of collateral drainage paths. Alternatively, the portals 28 can be formed such that the central core 20 is not intersected and the portals 28 are formed through the pairs of side walls 22 separating adjacent lumens 26. As shown in FIG. 10, a substantially similar technique is used to create portals 28 in a round implantable segment 10 having a central lumen in addition to the generally triangular shaped lumens 26. The dashed outline of the round implantable segment 10 illustrates the general shape of the round implantable segment 10 following the spreading of the device by the opposing wedge-shaped dies 134, 136. In the case of the flat implantable segment 110, the portals 128 are formed on each of the central cores 118 separately.

Figure 11:
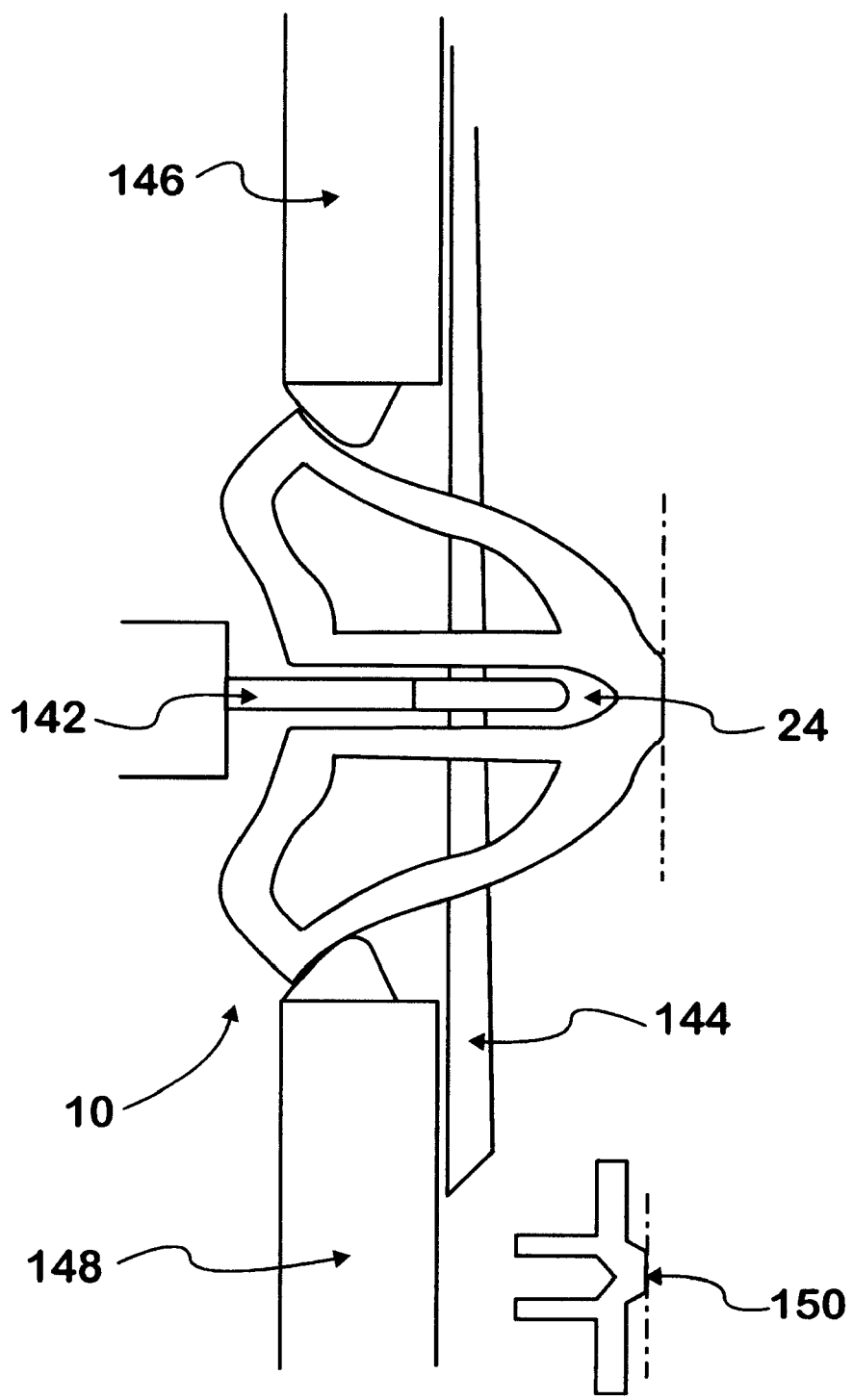
FIG. 11 is a partial cross-sectional view illustrating the positioning of a round implantable wound drain in preparation for the punching of portals.
Figure 12:
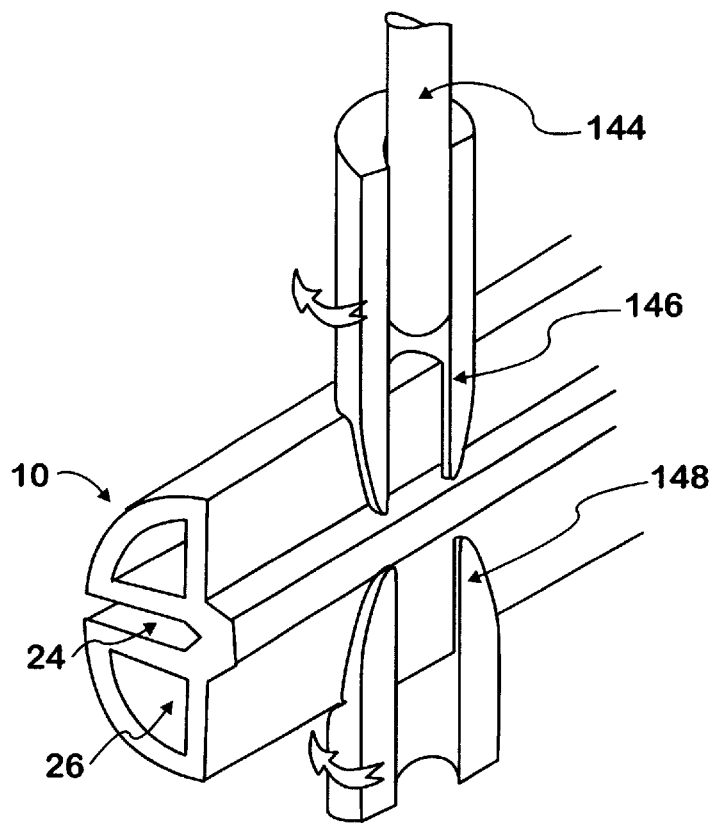
FIG. 12 is a cutaway isometric view illustrating the positioning of the punch with respect to the round implantable wound drain.
Figure 13:
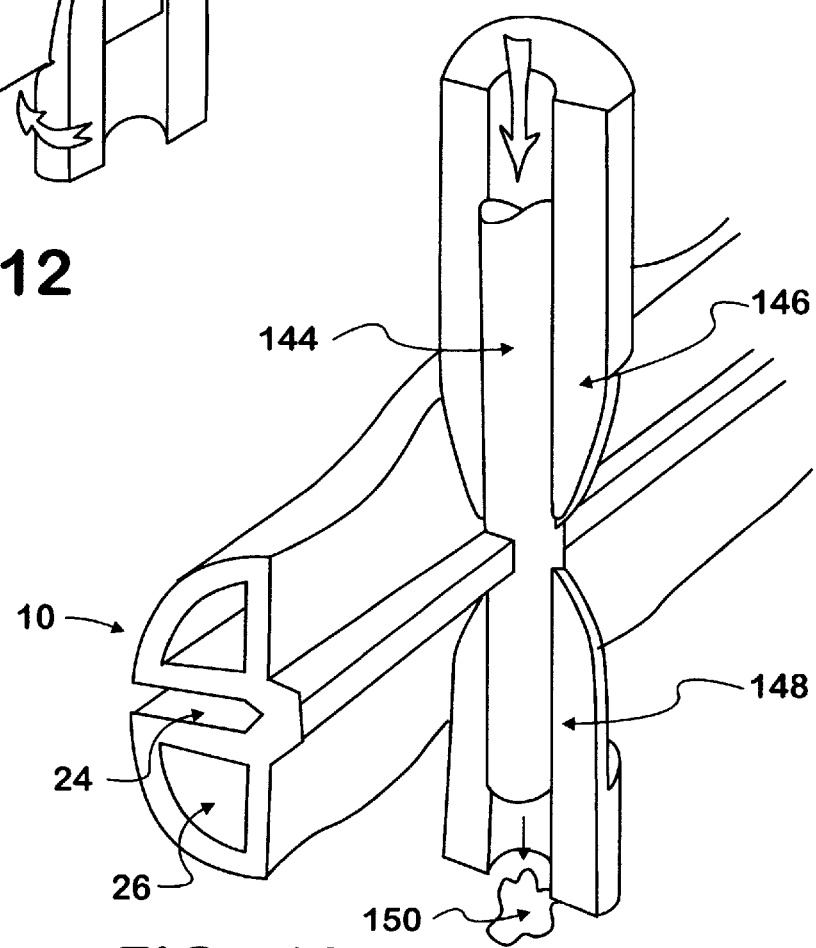
FIG. 13 is a cutaway isometric view illustrating the punching of portals in a round implantable wound drain.

An alternative technique for creating portals 28 in the round implantable segment 10 is shown in FIGS. 11 through 13. As shown in FIG. 11, the round implantable segment 10 is held in place by inserting stabilizing wings 142 in the horizontally situated ducts 24. The stabilizing wings 142 are provided with a relief in the middle to permit clearance of the punch 144. The vertical ducts 24 are maintained in position by a series of rails spaced between the portal 28 locations.

FIG. 12 illustrates the positioning of the punch 144 with respect to the round implantation wound drain and FIG. 13 illustrates the punching of portals in the round implantable wound drain. At the portal locations, an upper spreader tine 146 and a lower spreader tine 148 are attached to a rotatable cylinder (not shown). The upper spreader tine 146 and the lower spreader tine 148 are inserted in the vertical ducts 24. The upper spreader tine 146 and the lower spreader tine 148 rotate between approximately 80° and approximately 110° from the plane of the vertical duct 24. The punch 144 is driven through the cylinder to create the portal 28. Air ejection is used to eject the portal plug 150. The punch 144 is then withdrawn from the duct 24 and the upper spreader tine 146 and the lower spreader tine 148 are aligned with the vertical plane bisecting the duct 24. This technique can also be applied to created portals in alternative embodiments of the round implantable segment 10 and alternative embodiments of the flat implantable segment 110.

While the invention has been described with specific embodiments, other alternatives, modifications and variations will be apparent to those skilled in the art. Accordingly, it is intended to include all such alternatives, modifications and variations set forth within the spirit and scope of the appended claims.

What is claimed is:

1. A wound drain for connection to a suction source, comprising:
   a plurality of ducts;
   a plurality of lumens; and
   a plurality of portals providing fluid communication between the ducts and the lumens, where the portals are adapted and arranged to approximately provide uniform suction along the length of the wound drain; and
   wherein said portals are positioned relative to one another such that a first distance is defined by a longitudinal measurement between successive portals along the length of the wound drain at the proximal end, and a second distance is defined by a longitudinal measurement between successive portals along the length of the wound drain at the distal end; and
   wherein said first distance is greater than said second distance.

2. The wound drain of claim 1 wherein the portals are arranged in sets of portals where the portals in each set are the same size and where the sets of portals closer to a suction source are smaller than the sets of portals further away from a suction source.

3. The wound drain of claim 2 wherein each set of portals comprises two adjacent portals.

4. The wound drain of claim 1 wherein the lumens have a generally triangular cross-sectional shape.

5. The wound drain of claim 1 wherein the wound drain has a generally circular cross sectional shape.

6. The wound drain of claim 5 wherein the plurality of portals comprises eight portals.

7. The wound drain of claim 6 wherein each portal to lumen hole has a hydraulic diameter ($d_{hole}$) (in inches) determined in accordance with the following:

$$d_{hole}=0.5482(A/P)+(6.4852\times10^{-4})(A/P)(L_T-L)^3$$

where:

A is a cross-sectional area of the lumen (in inches$^2$),

P is a perimeter of the lumen (in inches), $L_T$ is a length of the wound drain (in inches), and L is a length between an end of the wound drain further away from a suction source and a center of the portal (in inches).

8. The wound drain of claim 7 wherein each portal has a portal diameter ($d_{portal}$)(in inches) determined in accordance with the following:

$$d_{portal}=0.015+3.49(T_{iw})+0.9(d_{hole}),$$

where:

$d_{hole}$ is the hydralic diameter of the portal (in inches), and $T_{iw}$ is a thickness of a wall between the duct and the adjacent lumen (in inches).

9. The wound drain of claim 1 further including a central core having a central longitudinal axis parallel to a longitudinal axis of the wound drain, the central core being positioned within the wound drain such that the central longitudinal axis runs along the center of the wound drain.

10. The wound drain of claim 9 wherein the central core defines a central lumen extending the length of the central core.

11. The wound drain of claim 9 wherein the central core defines a square lumen having a generally square shaped cross-section wherein the square lumen runs the length of the central core.

12. The wound drain of claim 1 wherein the plurality of lumens include four triangular lumens having a generally triangular cross-sectional shape and two square lumens having a generally square cross-sectional shape wherein each square lumen is positioned between two triangular lumens.

13. The wound drain of claim 1 wherein the wound drain has a generally oblong cross sectional shape.

14. The wound drain of claim 13 wherein the plurality of portals comprises twelve portals.

15. The wound drain of claim 14 wherein each portal to lumen hole has a hydraulic diameter ($d_{hole}$)(in inches) determined in accordance with the following:

$$d_{hole} = \frac{0.1823(P_S/A_S)^{0.5}}{L^{0.63}},$$

where:

$A_S$ is a cross-sectional area of the square lumen (in inches$^2$), $P_S$ is a perimeter of the square lumen (in inches), and L is a length between an end of the wound drain further away from a suction source and a center of the portal (in inches).

16. The wound drain of claim 15 wherein each portal has a portal diameter ($d_{portal}$)(in inches) is determined in accordance with the following:

$$d_{portal}=3.2052(T_{iw})+0.866(d_{hole})$$

where:

$d_{hole}$ is the hydralic diameter of the portal (in inches), and $T_{iw}$ is a thickness of a wall between the duct and the adjacent lumen (in inches).

17. The wound drain of claim 1 wherein each duct further comprises a duct entrance and a duct base wherein the width of the duct entrance is narrower than the width of the duct base.

18. The wound drain of claim 1 wherein each duct is in fluid communication with each of the lumens.

19. The wound drain of claim 1 wherein each duct is in fluid communication with the adjacent lumens.

20. The wound drain of claim 1 where the wound drain is manufactured from a pliable material.

21. The wound drain of claim 1 wherein the wound drain is manufactured from a plastic material.

22. The wound drain of claim 1 wherein the wound drain is manufactured from a silicone material.

23. The wound drain of claim 1 wherein the wound drain is manufactured using a material which has a hardness ranging from about 40 Shore A to about 70 Shore A.

24. A wound drain for colon to a suction source, comprising:

a plurality of duct;

a plurality of lumens; and a plurality of portals providing fluid communication between the ducts and the lumens wherein said portals are positioned relative to one another such that a first distance is defined as a longitudinal measurement between successive portals along the length of the wound drain at the proximal end, and a second distance is defined as a longitudinal measurement between successive portals along the length of the wound drain at the distal end; and wherein said first distance is greater than said second distance.

25. The wound drain of claim 24 wherein the lumens have a generally triangular cross-sectional shape.

26. The wound drain of claim 24 wherein the wound drain has a generally circular cross-sectional shape.

27. The wound drain of claim 24 further including a central core having a central longitudinal axis parallel to a longitudinal axis of the wound drain, the central core being positioned within the wound drain such that the central longitudinal axis runs along the center of the wound drain.

28. The wound drain of claim 27 wherein the central core defines a central lumen extending the length of the central core.

29. The wound drain of claim 27 wherein the central core defines a square lumen having a generally square shaped cross-section wherein the square lumen runs the length of the central core.

30. The wound drain of claim 24 wherein the wound drain has a generally oblong cross-sectional shape.

31. The wound drain of claim 24 wherein the plurality of lumens include four triangular lumens having a generally triangular cross-sectional shape and two square lumens having a generally square cross-sectional shape wherein each square lumen is positioned between two triangular lumens.

32. The wound drain of claim 24 wherein each duct further comprises a duct entrance and a duct base wherein the width of the duct entrance is narrower than the width of the duct base.

33. The wound drain of claim 24 wherein each duct is in fluid communication with each of the lumens.

34. The wound drain of claim 24 wherein each duct is in fluid communication with the adjacent lumens.

35. The wound drain of claim 24 where the wound drain is manufactured from a pliable material.

36. The wound drain of claim 24 wherein the wound drain is manufactured from a plastic material.

37. The wound drain of claim 24 wherein the wound drain is manufactured from a silicone material.

38. The wound drain of claim 24 wherein the wound drain is manufactured using a material which has a hardness ranging from about 40 Shore A to about 70 Shore A.

39. A wound drain for connection to a suction source, comprising:

a plurality of ducts;

a plurality of lumens; and a plurality of portals providing fluid communication between the ducts and the lumens where the ponds are adapted to approximately provide uniform suction along the length of the wound drain, and wherein each portal has a size and the size of portals are related to one another such that portals located along the length of the wound drain closer to a suction source have a first size, and portals located along the length of the wound drain away from a suction source have a second size; and wherein said first size is smaller than said second size.

40. The wound drain of claim 39 wherein the portals are arranged in sets of portals where the portals in each set are the same size and where the sets of portals closer to a suction source are smaller than the sets of portals further away from a suction source.

41. The wound drain of claim 40 wherein each set of portals comprises two adjacent portals.

42. The wound drain of claim 39 wherein the lumens have a generally triangular cross-sectional shape.

43. The wound drain of claim 39 wherein the wound drain has a generally circular cross-sectional shape.

44. The wound drain of claim 43 wherein the plurality of portals comprise eight portals.

45. The wound drain of claim 44 wherein each portal to lumen hole has a hydraulic diameter ($d_{hole}$)(in inches) determined in accordance with the following:

$$d_{hole}=0.5482(A/P)+(6.4852\times10^{-4})(A/P)(L_T-L)^3$$

where:

A is a cross-sectional area of the lumen (in inches$^2$),

P is a perimeter of the lumen (in inches), $L_T$ is a length of the wound drain (in inches), and L is a length between an end of the wound drain further away from a suction source and a center of the portal (in inches).

46. The wound drain of claim 45 wherein each portal has a portal diameter ($d_{portal}$)(in inches) determined in accordance with the following:

$$d_{portal}=0.015+3.49(T_{iw})+0.9(d_{hole}),$$

where:

$d_{hole}$ is the hydralic diameter of the portal (in inches), and $T_{iw}$ is a thickness of a wall between the duct and the adjacent lumen (in inches).

47. The wound drain of claim 39 further including a central core having a central longitudinal axis parallel to a longitudinal axis of the wound drain, the central core being positioned within the wound drain such that the central longitudinal axis runs along the center of the wound drain.

48. The wound drain of claim 47 wherein the central core defines a central lumen extending the length of the central core.

49. The wound drain of claim 47 wherein the central core defines a square lumen having a generally square shaped cross-section wherein the square lumen runs the length of the central core.

50. The wound drain of claim 39 wherein the plurality of lumens include four triangular lumens having a generally triangular cross-sectional shape and two square lumens having a generally square cross-sectional shape wherein each square lumen is positioned between two triangular lumens.

51. The wound drain of claim 39 wherein the wound drain has a generally oblong cross-sectional shape.

52. The wound drain of claim 51 wherein the plurality of portals comprise twelve portals.

53. The wound drain of claim 52 wherein each portal to lumen hole has a hydraulic diameter ($d_{hole}$)(in inches) determined in accordance with the following:

$$d_{hole}=\frac{0.1823\left(P_S/A_S\right)^{0.5}}{L^{0.63}}$$

where:

$A_S$ is a cross-sectional area of the square lumen (in inches$^2$), $P_S$ is a perimeter of the square lumen (in inches), and L is a length between an end of the wound drain further away from a suction source and a center of the portal (in inches).

54. The wound drain of claim 53 wherein each portal has a portal diameter ($d_{portal}$) (in inches) determined in accordance with the following:

$$d_{portal}=3.2052(T_{iw})+0.866(d_{hole})$$

where:

$d_{hole}$ is the hydralic diameter of the portal (in inches), and $T_{iw}$ is a thickness of a wall between the duct and the adjacent lumen (in inches).

55. The wound drain of claim 39 wherein each duct further comprises a duct entrance and a duct base wherein the width of the duct entrance is narrower than the width of the duct base.

56. The wound drain of claim 39 wherein each duct is in fluid communication with each of the lumens.

57. The wound drain of claim 39 wherein each duct is in fluid communication with the adjacent lumens.

58. The wound drain of claim 39 where the wound drain is manufactured from a pliable material.

59. The wound drain of claim 39 wherein the wound drain is manufactured from a plastic material.

60. The wound drain of claim 39 wherein the wound drain is manufactured from a silicone material.

61. The wound drain of claim 39 wherein the wound drain is manufactured using a material which has a hardness ranging from about 40 Shore A to about 70 Shore A.

* * * * *